United States Patent
Chen

(10) Patent No.: US 11,801,171 B2
(45) Date of Patent: Oct. 31, 2023

(54) DEFECATION DETECTION DEVICE

(71) Applicant: I-Ding Medical Equipment Co., Ltd., Kaohsiung (TW)

(72) Inventor: Hung Chi Chen, Kaohsiung (TW)

(73) Assignee: I-DING MEDICAL EQUIPMENT CO., LTD., Kaohsiung (TW)

( * ) Notice: Subject to any disclaimer, the term of this patent is extended or adjusted under 35 U.S.C. 154(b) by 165 days.

(21) Appl. No.: 17/562,906

(22) Filed: Dec. 27, 2021

(65) Prior Publication Data

US 2022/0323263 A1   Oct. 13, 2022

(30) Foreign Application Priority Data

Apr. 12, 2021   (TW) .................................. 110113090

(51) Int. Cl.
*A61F 13/42*        (2006.01)
*G01N 27/04*        (2006.01)
(Continued)

(52) U.S. Cl.
CPC .............. *A61F 13/42* (2013.01); *G01N 27/04* (2013.01); *A61F 2013/424* (2013.01); *H04W 4/38* (2018.02); *H04W 84/12* (2013.01)

(58) Field of Classification Search
CPC .... A61F 13/42; A61F 2013/424; A61F 5/451; A61F 5/4404; A61F 5/44; G01N 27/04; H04W 4/38; H04W 84/01
See application file for complete search history.

(56) References Cited

U.S. PATENT DOCUMENTS 6,149,636 A  * 11/2000 Roe .................... A61L 15/56
                                                    604/385.12
6,246,330 B1 *  6/2001 Nielsen ................ A61F 13/42
                                                       340/384.1
(Continued)

FOREIGN PATENT DOCUMENTS

CN       107296688 B      2/2021
EP         3260096 A1 * 12/2017  ........... A61B 5/6808
(Continued)

OTHER PUBLICATIONS

Search Report appended to an Office Action, which was issued to Taiwanese counterpart application No. 110113090 by the TIPO dated Jun. 7, 2021, with an English translation thereof.
(Continued)

*Primary Examiner* — Susan S Su
*Assistant Examiner* — Ted Yang
(74) *Attorney, Agent, or Firm* — Muncy, Geissler, Olds & Lowe, P.C.

(57) ABSTRACT

A defecation detection device (2) is adapted to communicate with a receiver (4) and includes a mounting seat (21), a resilient member (22) having a fixed end (221) that is connected to the mounting seat (21) and a free end (222) that is spaced apart from the mounting seat (21), a first conductive sheet (51) that is disposed on the free end (222) of the resilient member (22), a second conductive sheet (52) that is disposed on the mounting surface (211) of the mounting seat (21), and a transmitter module (6). When the free end (222) of the resilient member (22) is pressed to move toward the mounting seat (21), the first conductive sheet (51) is in contact with the second conductive sheet (52), and the transmitter module (6) is configured to wirelessly transmit a signal to the receiver (4) to allow the receiver (4) to output a notification.

11 Claims, 6 Drawing Sheets

(51) Int. Cl.
*H04W 84/12* (2009.01)
*H04W 4/38* (2018.01)

(56) References Cited

U.S. PATENT DOCUMENTS

| | | | | |
|---|---|---|---|---|
| 6,407,308 | B1* | 6/2002 | Roe | A61L 15/18 |
| | | | | 604/362 |
| 7,250,547 | B1* | 7/2007 | Hofmeister | G01N 27/121 |
| | | | | 340/573.5 |
| 10,722,405 | B2* | 7/2020 | Pepin | A61F 13/42 |
| 11,241,578 | B2* | 2/2022 | Naitoh | A61F 5/44 |
| 2003/0011479 | A1* | 1/2003 | Bluteau | A61F 13/42 |
| | | | | 340/573.5 |
| 2005/0102735 | A1* | 5/2005 | Popp | A41B 9/001 |
| | | | | 2/400 |
| 2011/0172625 | A1* | 7/2011 | Wada | A61F 13/42 |
| | | | | 604/385.01 |
| 2012/0197224 | A1* | 8/2012 | Chagger | A61F 13/42 |
| | | | | 604/361 |
| 2013/0072888 | A1* | 3/2013 | Zorin | A61F 13/72 |
| | | | | 28/100 |
| 2014/0266734 | A1* | 9/2014 | Chen | A61F 13/42 |
| | | | | 340/573.5 |
| 2014/0371702 | A1* | 12/2014 | Bosaeus | A61F 13/51484 |
| | | | | 604/385.01 |
| 2015/0245958 | A1* | 9/2015 | Chmielewski | A61F 13/535 |
| | | | | 604/385.201 |
| 2015/0282993 | A1* | 10/2015 | Lin | A61F 13/42 |
| | | | | 604/361 |
| 2016/0125759 | A1* | 5/2016 | Dougherty | G09B 19/0076 |
| | | | | 434/236 |
| 2016/0278990 | A1* | 9/2016 | Chen | A61B 5/6808 |
| 2017/0035622 | A1* | 2/2017 | Wang | A61F 13/42 |
| 2017/0156594 | A1* | 6/2017 | Stivoric | A61B 5/0008 |
| 2017/0296397 | A1* | 10/2017 | Kunze | A61F 13/42 |
| 2018/0036180 | A1* | 2/2018 | Long | A61F 13/49004 |
| 2018/0149635 | A1* | 5/2018 | Abir | A61F 13/42 |
| 2018/0253957 | A1* | 9/2018 | Jhangiani | G08B 21/20 |
| 2019/0282412 | A1* | 9/2019 | Decote | A61F 13/42 |
| 2019/0343695 | A1* | 11/2019 | Ide | A61F 13/49 |
| 2019/0374122 | A1* | 12/2019 | Kuenzi | A61B 5/6831 |
| 2020/0352794 | A1* | 11/2020 | Curran | A61F 13/42 |
| 2021/0121334 | A1* | 4/2021 | Sablone | A61F 13/15804 |
| 2022/0087876 | A1* | 3/2022 | Gu | A61F 13/49 |
| 2022/0133550 | A1* | 5/2022 | Chen | A61F 13/496 |
| | | | | 604/361 |

FOREIGN PATENT DOCUMENTS

| | | | | | |
|---|---|---|---|---|---|
| JP | H09294762 | A | * | 5/1996 | |
| JP | H09294762 | A | | 11/1997 | |
| JP | 2005000602 | A | | 1/2005 | |
| JP | 2009240758 | A | | 10/2009 | |
| JP | 2015002948 | A | | 1/2015 | |
| JP | 2016524161 | A | * | 8/2016 | |
| JP | 2016524161 | A | | 8/2016 | |
| JP | 2016182336 | A | | 10/2016 | |
| JP | 2017189615 | A | | 10/2017 | |
| TW | M402703 | U | | 5/2011 | |
| TW | M568118 | U | | 10/2018 | |
| WO | WO-2015003712 | A1 | * | 1/2015 | ............ A61F 13/42 |
| WO | 2020249725 | A1 | | 12/2020 | |
| WO | WO-2020249725 | A1 | * | 12/2020 | ............... A61B 5/72 |

OTHER PUBLICATIONS

Notice of Allowance issued to Japanese counterpart application No. 2022-026805 by the JPO dated May 17, 2023, with an English translation thereof.

* cited by examiner

DEFECATION DETECTION DEVICE

FIELD OF THE INVENTION

The disclosure relates to a detection device, and more particularly to a defecation detection device.

BACKGROUND OF THE INVENTION

Many elderly patients in care homes wear diapers and are cared for by caregivers. Although technological progress have led to the development of wetness indicators on the diapers so that a caregiver may be easily notified of a patient's need to change diapers, the applications of the wetness indicator are still limited, since the bodily functions of the patient include the need to both urinate and defecate. In cases where the patient defecates without any simultaneous urination, the wetness indicator on the diaper worn by the patient may not reliably indicate the need to change diapers, especially when the patient's stool is comparatively dry. Additionally, failure to promptly change the soiled diaper may cause significant health issues for the patient and affect the patient's quality of life.

BRIEF SUMMARY OF THE INVENTION

Therefore, an object of the disclosure is to provide a defecation detection device that can alleviate at least one of the drawbacks of the prior art.

According to the disclosure, the defecation detection device is used for detecting and notifying defecation in a diaper. The diaper has an inner surface and an outer surface, and is formed with a through hole through the inner surface and the outer surface. The defecation detection device is adapted to communicate with a receiver and includes a positioning member, a mounting seat, a resilient member, a first conductive sheet, a second conductive sheet, a transmitter module, a first electric wire, a second electric wire and a protection member. The positioning member is adapted to be removably mounted to the diaper and extends through the through hole of the diaper. The mounting seat has a mounting surface, and is mounted on the positioning member in a manner that the mounting seat is disposed inside the diaper when the positioning member is mounted to the diaper. The resilient member has a fixed end that is connected to the mounting seat, and a free end that is opposite to the fixed end and that is spaced apart from the mounting seat. The first conductive sheet is disposed on the free end of the resilient member, and faces the mounting seat. The second conductive sheet is disposed on the mounting surface of the mounting seat, and is spaced apart from the first conductive sheet. The transmitter module is removably mounted on the positioning member in a manner that the transmitter module is disposed outside the diaper when the positioning member is mounted on the diaper, and is configured to wirelessly communicate with the receiver. The first electric wire is adapted to extend through the through hole of the diaper, and has one end that is electrically connect to the first conductive sheet, and the other end that is electrically connected to the transmitter module in a removable connection. The second electric wire is adapted to extend through the through hole of the diaper, and has one end that is electrically connected to the second conductive sheet and the other end that is electrically connected to the transmitter module in a removable connection. The protection member is removably covering at least one side of the resilient member that is opposite to the mounting seat. When the free end of the resilient member is pressed to move toward the mounting seat, the first conductive sheet is in contact with the second conductive sheet, and the transmitter module is activated to wirelessly transmit a defecation detection signal to the receiver to allow the receiver to output a notification.

BRIEF DESCRIPTION OF THE DRAWINGS

Other features and advantages of the disclosure will become apparent in the following detailed description of the embodiments with reference to the accompanying drawings, of which.

DETAILED DESCRIPTION OF THE INVENTION

Figure 1:
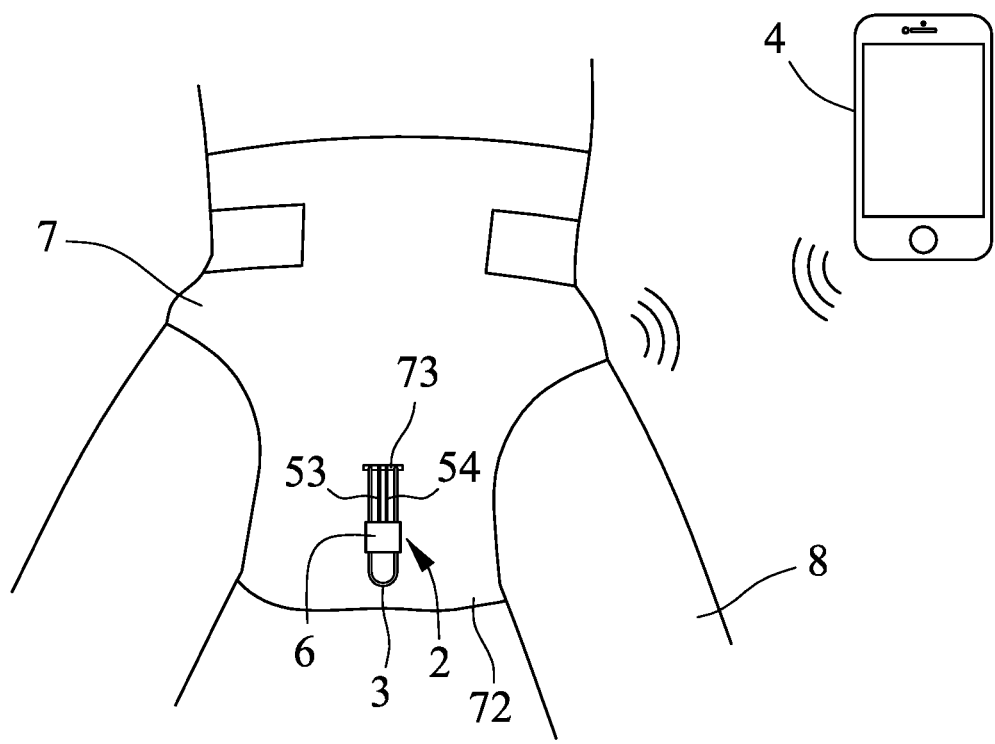
FIG. 1 is a schematic view illustrating a first embodiment of a defecation detection device according to this disclosure.

Before the disclosure is described in greater detail, it should be noted that where considered appropriate, reference numerals or terminal portions of reference numerals have been repeated among the figures to indicate corresponding or analogous elements, which may optionally have similar characteristics.

Referring to FIGS. 1 to 4, showing a defecation detection device 2 according to a first embodiment the present disclosure. The defecation detection device 2 is mounted to a diaper 7 worn by a wearer 8, and is used for detecting and notifying an occurrence of defecation in the diaper 7. The diaper 7 has an inner surface 71 and an outer surface 72, and is formed with a through hole 73 passing through the inner surface 71 and the outer surface 72. In the first embodiment, the defecation detection device 2 includes a mounting seat 21, a positioning member 3, a resilient member 22, a first conductive sheet 51, a second conductive sheet 52, a first electric wire 53, a second electric wire 54, a connector 55 and a transmitter module 6. Additionally, the defecation detection device 2 is also adapted to communicate with a receiver 4.

The positioning member 3 is removably mounted to the diaper 7 and extends through the through hole 73 (see FIG. 2), and the mounting seat 21 is mounted on the positioning member 3 in a manner that the mounting seat 21 is disposed inside the diaper 7 when the positioning member 3 is mounted to the diaper 7.

Figure 3:
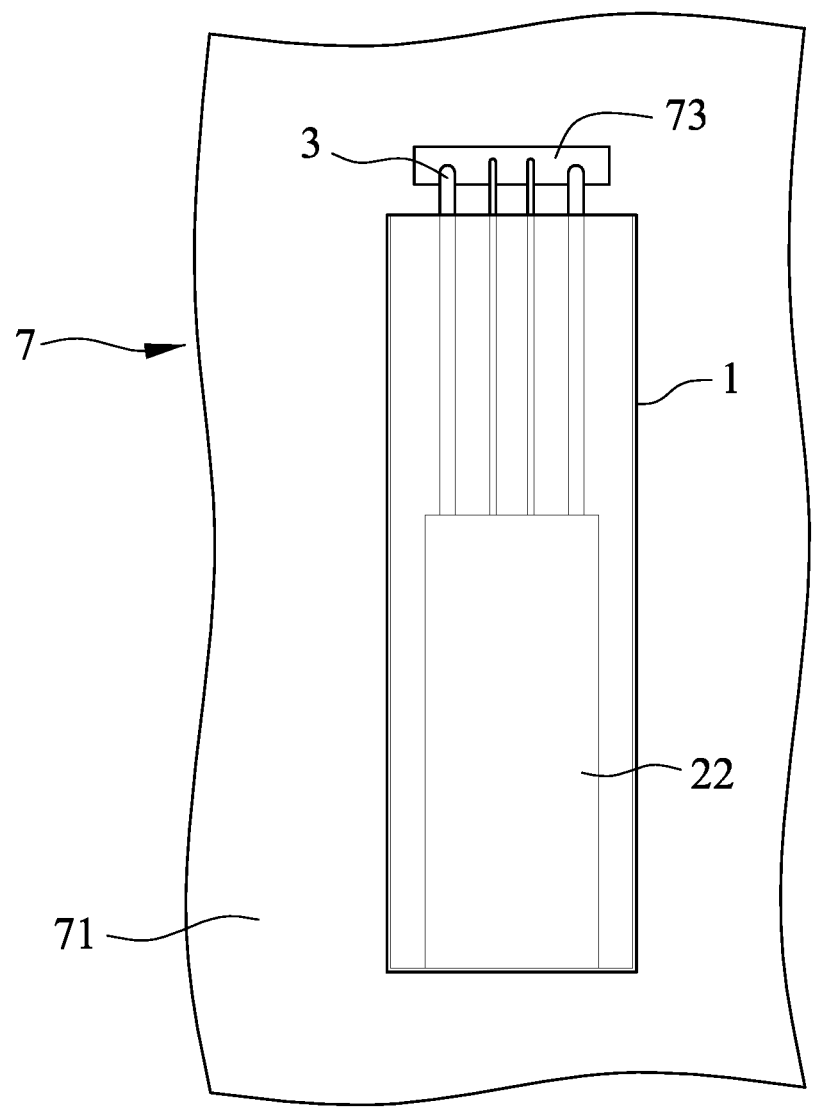
FIG. 3 is a side view of the first embodiment of the defecation detection device.

In the first embodiment, the mounting seat 21 has a mounting surface 211, and the positioning member 3 is a clip. The positioning member 3 includes a first portion 31 that is partially inserted into the mounting seat 21, a second portion 32 that curvedly extends from the first portion 31, and a third portion 33 that extends from the second portion 32. When the positioning member 3 clips to the diaper 7, the first portion is disposed on the inner surface 71 of the diaper 7, the mounting surface 211 of the mounting seat 21 faces away from the inner surface 71 of the diaper 7, the second portion 32 extends across the through hole 73, and the third portion 33 abuts against the outer surface 72 of the diaper 7. Referring to FIGS. 1 and 3, in the first embodiment, the positioning member 3 is designed to be a hollow frame for reduced weight, thereby decreasing the burden on the wearer 8.

Referring back to FIG. 2, the resilient member 22 is U-shaped, and has a fixed end 221 that is connected to the mounting seat 21, and a free and 222 that is opposite to the fixed end 221 and that is spaced apart from the mounting seat 21. In some embodiments, the resilient member 22 and the mounting seat 21 is formed in one piece.

The first conductive sheet 51 is disposed on the free end 222 of the resilient member 22, and faces the mounting seat 21. The second conductive sheet 52 is disposed on the mounting surface 211 of the mounting seat 21, and is spaced apart from the first conductive sheet 51.

The transmitter module 6 is removably mounted on the positioning member 3 in a manner that the transmitter module 6 is disposed outside the diaper 7 when the positioning member 3 is mounted on the diaper 7, and is configured to wirelessly communicate with the receiver 4. More specifically, the transmitter module 6 is removably mounted to the third portion 33 of the positioning member 3, and includes an input port and other components such as a processor, a wireless transmitter, a battery, etc. (not shown).

The first electric wire 53 extends along the positioning member 3 and through the through hole 73 of the diaper 7, and has one end that is electrically connected to the first conductive sheet 51, and the other end that is electrically connected to the transmitter module 6 in a removable connection. The second electric wire 54 also extends along the positioning member 3 and through the through hole 73 of the diaper 7, and has one end that is electrically connected to the second conductive sheet 52 and the other end that is electrically connected to the transmitter module 6 in a removable connection. More specifically, the other end of the first electric wire 53 and the other end of the second electric wire 54 are both connected to the connector 55, and the first and second electric wires 53, 54 are connected to the connector 55 in a manner that the other end of the first electric wire 53 and the other end of the second electric wire 54 are insulated from each other. In other words, the connector 55 gathers the first and second electric wires 53, 54 and electrically connects to the input port 61 of the transmitter module 6 by being inserted into the input port 61, so that both the first and second electric wires 53, 54 are electrically connected to the transmitter module 6 while being insulated from each other.

Figure 2:
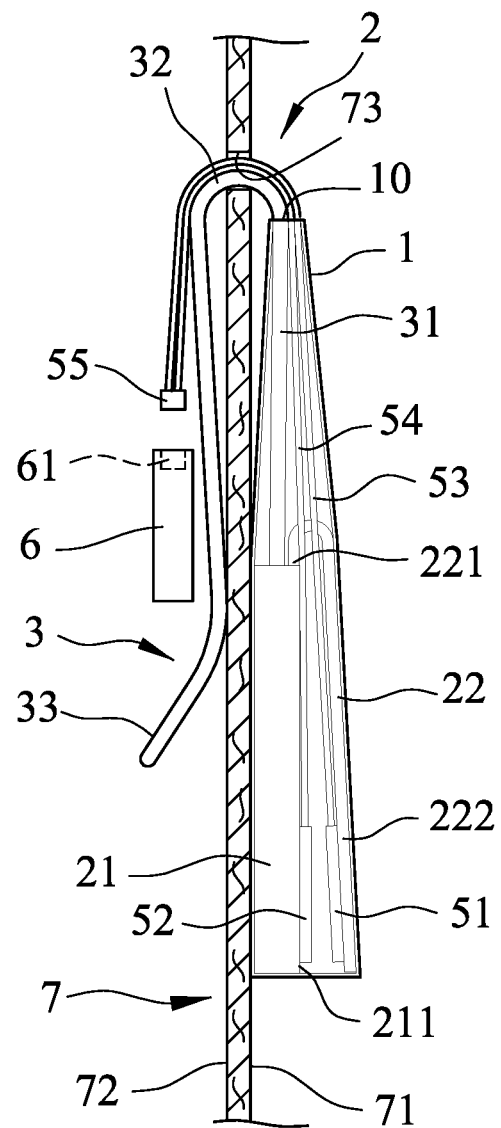
FIG. 2 is a sectional view of the first embodiment of the defecation detection device mounted to a diaper.

The defecation detection device 2 further includes a protection member 1 removably covering at least one side of the resilient member 22 that is opposite to the mounting seat 21. Referring to FIG. 2, in the first embodiment, the protection member 1 is a bag removably covering over and protecting the mounting seat 21, the resilient member 22, the first conductive sheet 51, the second conductive sheet 52, a portion of the first electric wire 53, a portion of the second electric wire 54 and the first portion 31 of the positioning member 3. When the wearer 8 wearing the diaper 7 defecates, faeces 81 expelled by the wearer 8 (see FIG. 4) will soil the inner surface 71 of the diaper 7. However, because the above-mentioned components of the defecation detection device 2 are covered by the protection member 1, they are protected against contamination by the faeces 81. It should be noted, however, that this is not a limitation, and in other embodiments according to this disclosure the protection member 1 does not cover the first portion 31 of the positioning member 3 (see FIG. 5). Additionally, it should also be noted that in the first embodiment, the protection member 1 may be a re-sealable plastic bag such as a zip-lock bag. Moreover, the protection member 1 has an opening 10, and is waterproof which will prevent moisture sensitive components of the defecation detection device 2 such as the mounting seat 21, the resilient member 22, the first and second conductive metal sheets 51, 52 from being damaged in cases where the faeces of the wearer 8 happens to be more watery, or if the wearer 8 urinates while wearing the diaper 7.

Referring to FIG. 1, in this embodiment, the receiver 4 may be a portable device such as a smartphone or a tablet, and the transmitter module 6 is configured to use a wireless technology such as Wi-Fi, Bluetooth® or radio-frequency identification (RFID) to communicate with the receiver 4. Additionally, a computer or smartphone software application with defecation notification functionality may be installed on the receiver 4 to more efficiently notify a caregivers.

Figure 4:
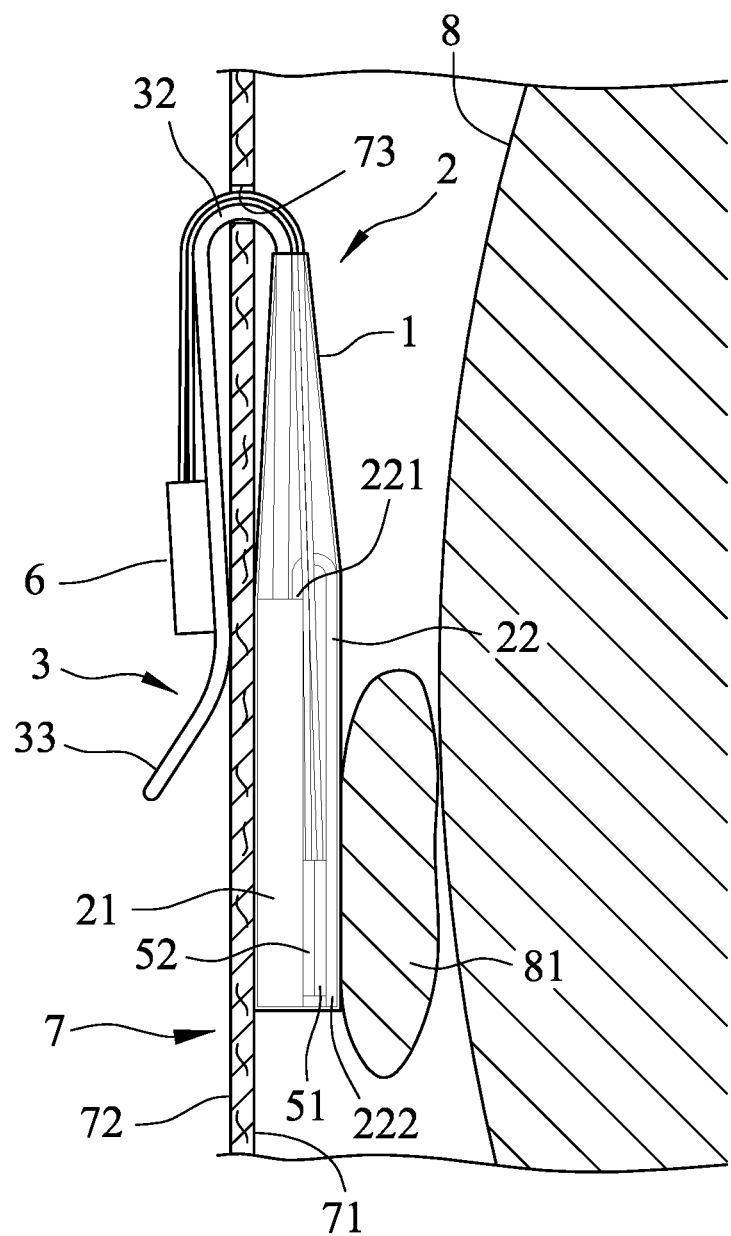
FIG. 4 is a fragmentary sectional view illustrating the first embodiment of the defecation detection device interacting with a wearer's faeces.
Figure 5:
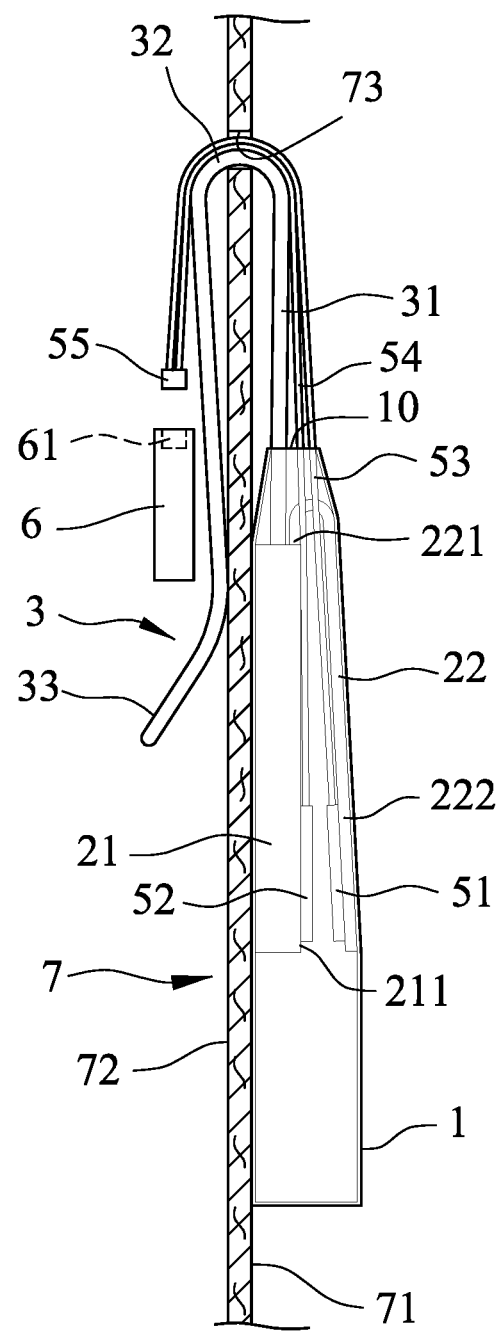
FIG. 5 is a sectional view illustrating a variation of the first embodiment of the defecation detection device according to this disclosure.

In use, the defecation detection device 2 is mounted to the diaper 7 of the wearer 8 by the caregivers. The mounting seat 21, the resilient member 22, the first conductive sheet 51, the second conductive sheet 52, and a portion of the positioning member 3 are first put into the protection member 1, which is a re-sealable plastic zip-lock bag, through the opening 10. The opening 10 of the protection member 1 is now positioned roughly between the first portion 31 and the second portion 32 of the positioning member 3, and then the opening 10 is sealed by the caregiver, thereby protecting the mounting seat 21, the resilient member 21, the first conductive sheet 51, the second conductive sheet 52, the first portion 31 of the positioning member 3, and a portion of the first and second electric wires 53, 54. Subsequently, the caregiver operates the third portion 33 of the positioning member 3, beginning from the inner surface 71 of the diaper 7 and threading the third portion 33 through the through hole 73 until the second portion 32 of the positioning member 3 extends across the through hole 73, and the third portion abuts against the outer surface 72 of the diaper 7. Through this action, the other ends of both the first and second electric wires 53, 54 that extend along the positioning member 3 are also threaded through the through hole 73 to be on the outer surface 72 side of the diaper 7, and the mounting seat 21 will be enclosed by the protection member 1 while it abuts against the inner surface 71 of the diaper 7. Afterwards the connector 55 is inserted into the input port 61 of the transmitter module 6, and the transmitter module 6 is removably disposed on the positioning member 3 (as shown in FIG. 4). For example, the transmitter module 6 may be attached to the third portion 33 of the positioning member 3 by magnets, hook-and-loop fasteners, etc.

Referring to FIGS. 1 and 4, when the wearer 8 wearing the diaper 7 mounted with the defecation detection device 2 defecates, the faeces 81 expelled by the wearer 8 will be constrained between the diaper 7 and the body of the wearer 8. The presence of the faeces 81 will press and cause the free end 222 of the resilient member 3 to move toward the mounting seat 21, and cause the first conductive sheet 51 on the free end 222 to be in contact with the second conductive sheet on the mounting seat 21 to form a closed circuit among components of the transmitter module 6 (e.g., the wireless transmitter, the battery, etc.), whereupon the transmitter module will be activated to transmit a defecation detection signal to the receiver 4. When the receiver 4 receives the defecation detection signal transmitted by the transmitter module 6, the software application of the receiver 4 will process the defecation detection signal and output a notification to alert the caregiver equipped with the receiver 4, and inform the caregiver that the wearer 8 has defecated and that a diaper change for the wearer 8 should be arranged. For example, the notification outputted by the receiver 4 may be in a form of vibration, sound, a message, or a combination thereof.

Figure 6:
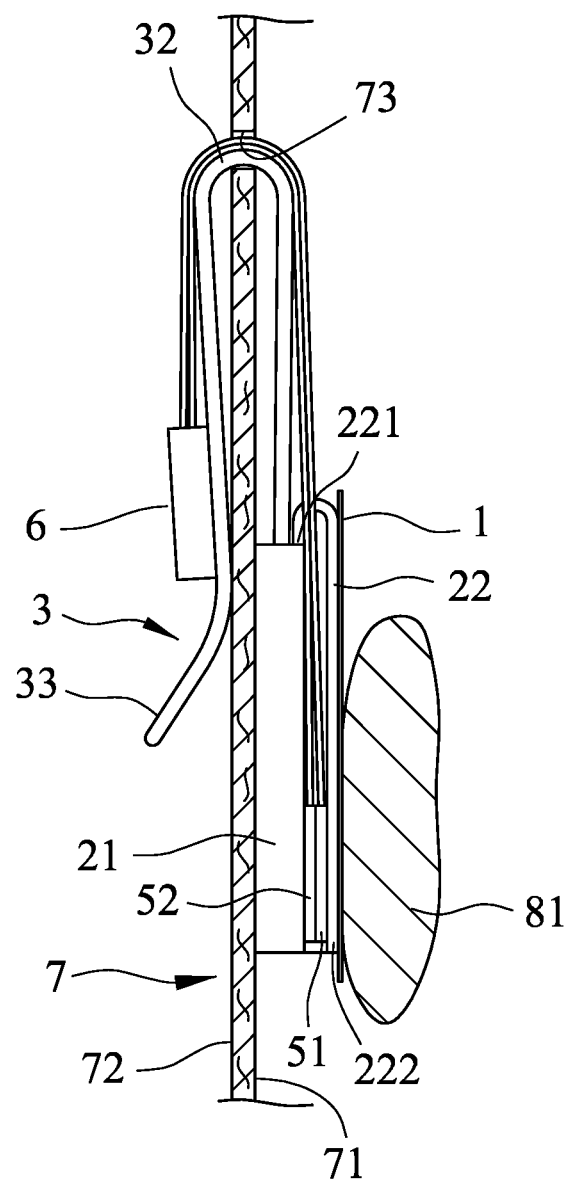
FIG. 6 is a sectional view illustrating a second embodiment of the defecation detection device according to the present disclosure.

Referring to FIG. 6, a second embodiment of the defecation detection device 2 is shown. The second embodiment is structurally similar to the first embodiment except for the protection member 1, which in the second embodiment is a protection sheet that is removably mounted on one side of the resilient member 22, and covers and protects the resilient member 22 from being contaminated by the faeces 81. Additionally, it should be noted that the protection member 1 can be sanitised for repeat use.

In summary of the above, the defecation detection device 2 according to this disclosure has at least the following advantages and effects:

1. By disposing the resilient member 22 on the mounting seat 21, the first conductive sheet 51 on the free end 222 of the resilient member 22, and the second conductive sheet 52 on the mounting seat 21, the defecation detection device 2 according to this disclosure is able to detect defecation.
2. When the defecation detection device 2 has detected an occurrence of defecation, the transmitter module 6 will wirelessly transmit the defecation detection signal to the receiver 4, so that the receiver 4 may alert the caregiver.
3. In the first embodiment, the protection member 1 may be used repeatedly after sanitation, and is removably covering over and protecting components such as the mounting seat 21, the resilient member 22, the first conductive sheet 51, the second conductive sheet 52, a portion of the first electric wire 53, a portion of the second electric wire 54. The components are therefore protected from contamination by the faeces 81. Additionally, the protection member 1 is waterproof which can shield the components from moisture when the wearer 8 urinates in the diaper 7.
4. In the second embodiment, the protection member 1 may is reusable after sanitation, and is removably mounted on one side of the resilient member 22. The protection member 1 of the second embodiment can prevent the resilient member 22 from being contaminated by the faeces 81.

Therefore, the object of the disclosure is satisfied.

In the description above, for the purposes of explanation, numerous specific details have been set forth in order to provide a thorough understanding of the embodiments. It will be apparent, however, to one skilled in the art, that one or more other embodiments may be practiced without some of these specific details. It should also be appreciated that reference throughout this specification to "one embodiment," "an embodiment," an embodiment with an indication of an ordinal number and so forth means that a particular feature, structure, or characteristic may be included in the practice of the disclosure. It should be further appreciated that in the description, various features are sometimes grouped together in a single embodiment, figure, or description thereof for the purpose of streamlining the disclosure and aiding in the understanding of various inventive aspects, and that one or more features or specific details from one embodiment may be practiced together with one or more features or specific details from another embodiment, where appropriate, in the practice of the disclosure.

I claim:

1. A defecation detection device (2) for detecting and notifying defecation in a diaper (7) that has an inner surface (71) and an outer surface (72), that is formed with a through hole (73) through the inner surface (71) and the outer surface (72), said defecation detection device being adapted to communicate with a receiver (4) and characterised by:
    a positioning member (3) being adapted to be removably mounted to the diaper (7) and extend through the through hole (73) of the diaper (7);
    a mounting seat (21) having a mounting surface (211), and being mounted on said positioning member (3) in a manner that said mounting seat (21) is disposed inside the diaper (7) when said positioning member (3) is mounted to the diaper (7);
    a resilient member (22) having a fixed end (221) that is connected to said mounting seat (21), and a free end (222) that is opposite to said fixed end (221) and that is spaced apart from said mounting seat (21);
    a first conductive sheet (51) disposed on said free end (222) of said resilient member (22) and facing said mounting seat (21);
    a second conductive sheet (52) disposed on said mounting surface (211) of said mounting seat (21), and spaced apart from said first conductive sheet (51);
    a transmitter module (6) removably mounted on said positioning member (3) in a manner that said transmitter module (6) is disposed outside the diaper (7) when said positioning member (3) is mounted on the diaper (7), and configured to wirelessly communicate with the receiver (4);
    a first electric wire (53) being adapted to extend through the through hole (73) of the diaper (7), and having one end that is electrically connected to said first conductive sheet (51), and the other end that is electrically connected to said transmitter module (6) in a removable connection;
    a second electric wire (54) being adapted to extend through the through hole (73) of the diaper (7), and having one end that is electrically connected to said second conductive sheet (52) and the other end that is electrically connected to said transmitter module (6) in a removable connection; and
    a protection member (1) removably covering at least one side of said resilient member (22) that is opposite to said mounting seat (21),
    wherein, when said free end (222) of said resilient member (22) is pressed to move toward said mounting seat (21), said first conductive sheet (51) is in contact with said second conductive sheet (52), and said transmitter module (6) is activated to wirelessly transmit a defecation detection signal to the receiver (4) to allow the receiver (4) to output a notification.

2. The defecation detection device as claimed in claim 1, wherein said protection member (1) is a bag removably covering over and protecting said mounting seat (21), said resilient member (22), said first conductive sheet (51), said second conductive sheet (52), a portion of said first electric wire (53), and a portion of said second electric wire (54).

3. The defecation detection device as claimed in claim 2, wherein said protection member (1) is a re-sealable plastic bag.

4. The defecation detection device as claimed in claim 1, wherein said resilient member (22) and said mounting seat (21) is formed in one piece.

5. The defecation detection device as claimed in claim 1, wherein said transmitter module (6) is configured to use a wireless technology of Wi-Fi to transmit the defecation detection signal to the receiver (4).

6. The defecation detection device as claimed in claim 1, wherein said transmitter module (6) is configured to use a wireless technology of Bluetooth® to transmit the defecation detection signal to the receiver (4).

7. The defecation detection device as claimed in claim 1, wherein said transmitter module (6) is configured to use a wireless technology of radio-frequency identification to transmit the defecation detection signal to the receiver (4).

8. The defecation detection device as claimed in claim 1, characterised by:
    a connector (55), to which said the other end of said first electric wire (53) and said the other end of said second electric wire (54) are connected in a manner that said the other end of said first electric wire (53) and said the other end of said second electric wire (54) are insulated from each other,
        wherein said transmitting module (6) includes an input port (61), and said connector (55) is inserted into said input port (61) so as to electrically connect said first electric wire (53) and second electric wire (54) to said transmitting module (6).

9. The defecation detection device as claimed in claim 1, wherein said protection member (1) is a protection sheet that does not cover a first portion (31) of the positioning member (3).

10. The defecation detection device as claimed in claim 1, wherein said protection member (1) is a protection sheet that is removably mounted on one side of said resilient member (22).

11. The defecation detection device as claimed in claim 1, wherein:
    said positioning member (3) is a clip, and includes a first portion (31) that is partially inserted into said mounting seat (21), a second portion (32) that curvedly extends from said first portion (31), and a third portion (33) that extends from said second portion (32);
    when said positioning member (3) clips to the diaper (7), said first portion (31) is disposed on the inner surface (71) of the diaper (7), said second portion (32) extends across the through hole (73), and said third potion (33) abuts against the outer surface (72) of the diaper (7); and said mounting surface (211) of said mounting seat (21) faces away from the inner surface (71) of the diaper (7).

\* \* \* \* \*